United States Patent
Threlkeld et al.

(10) Patent No.: US 7,271,325 B1
(45) Date of Patent: Sep. 18, 2007

(54) SOYBEAN CULTIVAR S06-WW157958

(75) Inventors: Kevin Threlkeld, Washington, IA (US); Julia L. Brown, Sidell, IL (US); Roger L. McBroom, St. Joseph, IL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 11/360,209

(22) Filed: Feb. 23, 2006

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. ............... 800/312; 800/260; 800/278; 800/279; 800/281; 800/284; 800/298; 800/300; 800/301; 800/302; 800/303; 435/415; 435/426

(58) Field of Classification Search ............... None
See application file for complete search history.

*Primary Examiner*—Russell P. Kallis
(74) *Attorney, Agent, or Firm*—Dana S Rewoldt (57) ABSTRACT

The present invention is in the field of soybean variety S06-WW157958 breeding and development. The present invention particularly relates to the soybean variety S06-WW157958 and its progeny, and methods of making S06-WW157958.

13 Claims, 2 Drawing Sheets

SOYBEAN CULTIVAR S06-WW157958

THE FIELD OF THE INVENTION

The present invention is in the field of soybean variety S06-WW157958 breeding and development. The present invention particularly relates to the soybean variety S06-WW157958 and its progeny, and methods of making.

BACKGROUND OF THE INVENTION

Soybean *Glycine max* (L) is an important oil seed crop and a valuable field crop. However, it began as a wild plant. This plant and a number of other plants have been developed into valuable agricultural crops through years of breeding and development. The pace of the development of soybeans, into an animal foodstuff and as an oil seed has dramatically increased in the last one hundred years. Planned programs of soybean breeding have increased the growth, yield and environmental hardiness of the soybean germplasm.

Due to the sexual reproduction traits of the soybean, the plant is basically self-pollinating. A self-pollinating plant permits pollen from one flower to be transferred to the same or another flower of the same plant. Cross-pollination occurs when the flower is pollinated with pollen from a different plant; however, soybean cross-pollination is a rare occurrence in nature.

Thus the growth and development of new soybean germplasm requires intervention by the breeder into the pollination of the soybean. The breeders' methods of intervening in the pollination depend on the type of trait that is being bred. Soybeans are developed for a number of different types of traits morphological (form and structure), phenotypical, or for traits like growth, day length, temperature requirements, initiation date of floral or reproductive development, fatty acid contents, insect resistance, herbicide resistance and yield. The genetic complexity of the trait often drives the selection of the breeding method.

Due to the number of genes within each chromosome, millions of genetic combinations exist in the breeders' experimental soybean material. This genetic diversity is so vast that a breeder cannot produce the same two cultivars twice using the exact same starting parental material. Thus, developing a single variety of useful commercial soybean germplasm is highly unpredictable, and requires intensive research and development.

The development of new soybeans comes through breeding techniques, such as: recurrent selection, mass selections, backcrossing, single seed descent and multiple seed procedure. Additionally, markers' assisted breeding allows more accurate movement of desired alleles or even specific genes or sections of chromosomes to be moved within the germplasm that the breeder is developing. RFLP, RAPD, AFLP, SSR, SNP, SCAR, isozymes, are all forms of markers that can be employed in breeding soybeans or in moving traits into soybean germplasm. Other breeding methods are known and are described in various soybean textbooks.

When a soybean variety is being employed to develop a new soybean variety or an improved variety the selection methods include backcrossing, pedigree breeding, recurrent selection, modified selection and mass selection. The efficiency of the breeding procedure along with the goal of the breeding is the factors for determining which selection techniques are employed. A breeder continuous evaluates the success of the breeding program and therefore the efficiency of any breeding procedure. The success is usually measured by yield increase, commercial appeal and environmental adaptability of the developed germplasm.

The development of new soybean cultivars most often requires the development of hybrid crosses (some exceptions being initial development of mutants directly through the use of the mutating agent, certain materials introgressed by markers, or transformants made directly through transformation methods) and the selection of progeny therefrom. Hybrids can be achieved by manual manipulation of the sexual organs of the soybean or by the use of male sterility systems. Breeders often try to identify true hybrids by a readily identifiable trait or the visual differences between Inbred and hybrid material. These heterozygous hybrids are then selected and repeatedly selfed and reselected to form new homozygous soybean lines.

Mass and recurrent selection can be used to improve populations. Several parents are intercrossed and plants are selected based on selected characteristics like superiority or excellent progeny. Outcrossing to a number of different parents creates fairly heterozygous breeding populations.

Pedigree breeding is commonly used with two parents that possess favorable, complementary traits. The parents are crossed to form a F1 hybrid. The progeny of the F1 hybrid is selected and the best individual F2s are selected; this selection process is repeated in the F3 and F4 generations. The inbreeding is carried forward and at F5-F7 the best lines are selected and tested in the development stage for potential usefulness in a selected geographic area.

In backcross breeding a genetic allele or loci is transferred into a desirable homozygous recurrent parent. The trait is in the donor parent and is tracked into the recurrent parent. The resultant plant is like the recurrent parent with the new desired allele or loci.

The single-seed descent method involves use of a segregating plant population for harvest of one seed per plant. Each seed sample is planted and the next generation is formed. When the F2 lines are advanced to F6 each plant will be derived from a different F2. The population will decline due to failure of some seeds, so not all F2 plants will be represented in the progeny.

New varieties must be tested thoroughly to compare their development with commercially available soybeans. This testing usually requires at least two years and up to six years of comparisons with other commercial soybeans. Varieties that lack the entire desirable package of traits can be used as parents in new populations for further selection or are simply discarded. The breeding and associated testing process is 8 to 12 years' of work prior to development of a new variety. Thousands of varietal lines are produced but only a few lines are selected in each step of the process. Thus the breeding system is like a funnel with numerous lines and selections in the first few years and fewer and fewer lines in the middle years until one line is selected for the final development testing.

The selected line or variety will be evaluated for its growth, development and yield. These traits of a soybean are a result of the variety's genetic potential interacting with its environment. All varieties have a maximum yield potential that is predetermined by its genetics. This hypothetical potential for yield is only obtained when the environmental conditions are perfect. Since prefect growth conditions do not exist, field experimentation is necessary to provide the environmental influence and to measure its effect on the development and yield of the soybean. The breeder attempts to select for good soybean yield potential under a number of different environmental conditions.

Selecting for good soybean yield potential in different environmental conditions is a process that requires planning based on the analysis of data in a number of seasons. Identification of the varieties carrying a superior combination of traits, which will give consistent yield potential, is a complex science. The desirable genotypic traits in the variety can often be masked by other plant traits, unusual weather patterns, diseases, and insect damage. One widely employed method of identifying a superior plant with such genotypic traits is to observe its performance relative to commercial and experimental plants in replicated studies. These types of studies give more certainty to the genetic potential and usefulness of the plant across a number of environments.

In summary, the goal of the soybean plant breeder is to produce new and unique soybeans and progeny of the soybeans for farmers' commercial crop production. To accomplish this the plant breeder painstakingly crosses two or more varieties or germplasm. Then the results of this cross are repeatedly selfed or backcrossed to produce new genetic patterns. Newer avenues for producing new and unique genetic alleles into soybeans include introducing mutations or transgenes into the genetic material of the soybean are now in practice in the breeding industry. These genetic alleles can alter pest resistance such as insect resistance, nematode resistance, herbicide resistance, or they can alter the plant's disease tolerance, or its fatty acid compositions, the amount of oil produced, and/or the amino acid compositions of the soybean plant or its seed.

The traits a breeder selects for when developing new soybeans are driven by the ultimate goal of the end user of the product. Thus if the goal of the end user is to resist a certain plant disease so overall more yield is achieved, then the breeder drives the introduction of genetic alleles and their selection based on disease resistant levels shown by the plant. On the other hand, if the goal is to produce a specific oil, with a high level of oleic acid and a lower level of linoleic acid, then the breeder may drive the selection of genetic alleles based on levels of fatty acids in the seed and accept some lesser yield potentials or other less desirable agronomic traits.

The new genetic alleles being introduced in to soybeans are widening the potential uses and markets for the various products and by-products of the oil from the seed plants such as soybean. A major product extracted from soybeans is the oil in the seed. Soybean oil is employed in a number of retail products such as cooking oil, baked goods, margarines and the like. Another useful product is soybean meal, which is a component of many foods and animal feedstuffs.

SUMMARY OF THE INVENTION

One embodiment of the invention relates to seed of a soybean cultivar designated S06-WW157958. The invention relates to the plant from the seed designated S06-WW157958, or the plant parts. The invention also encompasses a tissue culture of regenerable cells, cells or protoplasts being from a tissue selected from the leaf, pollen, stomatal cell, embryo, meristematic cell, root, root tip, anther, flower, ovule, seed, stem, pod, petal and the cells thereof.

The invention in one aspect covers a soybean plant, or parts thereof, having all of the physiological and morphological characteristics of the soybean plant.

Another aspect of this invention is the soybean plant seed or derived progeny which contains a transgene which provides herbicide resistance, insect resistance, resistance to disease, resistance to nematodes, male sterility, or which alters the oil profiles, the fatty acid profiles, the amino acids profiles or other nutritional qualities of the seed.

The present invention further covers a method for producing a soybean seed with the steps of crossing at least two parent soybean plants and harvesting the hybrid soybean seed, wherein at least one parent soybean plant is the present invention. In another aspect of the invention covers the hybrid soybean seed and the progeny soybean plant and resultant seed, or parts thereof from the hybrid seed or plant or its progeny.

In an additional aspect, the invention covers a method for producing a soybean progeny from the invention by crossing soybean line S06-WW157958 with a second soybean plant to yield progeny soybean seed and then growing progeny soybean seed.

Yet another aspect of the invention covers a method for a breeding program using plant breeding techniques which employ the soybean plant S06-WW157958 as plant breeding material and performing breeding by selection techniques, backcrossing, pedigree breeding, marker enhanced selection, mutation and transformation.

DETAILED DESCRIPTION

The following data is used to describe and enable the present soybean invention.

| Trait Code | Performance Trait Description |
|---|---|
| VHNO | Variety/Hybrid Number |
| YGSMN | Grain Yield at Std MST (standard moisture)-YGSMN |
| MRTYN | Maturity Days from planting MRTYN |
| HLDGR | Harvest Lodging HLDGR |
| PLHTN | Plant Height (cm) |
| PRR_R | *Phytophthora* Root Rot To PRR_R |
| IC_R | Iron Chlorosis IC_R |
| SDS_R | Sudden Death Syndrome SDS_R |
| SCL_R | *Sclerotinia* White Mold SCL_R |
| FELSR | Frogeye Leaf Spot FELSR |
| STR_R | Shattering STR_R |
| GLDGR | Green Lodging GLDGR |
| PLBRR | Plant Branching PLBRR |
| EMRGR | Emergence EMRGR |

Syngenta Soybean Data Collection Traits and Timing
Order 1 = Seedling, 2 = Vegetative, 3 = Reproductive to grain-fill, 4 = Maturity
Opportunistic ratings should only be collected if differences occur.
At least one variety has a rating of 5 or greater and there is a spread of 3 in the ratings.

| Order | Trait Group | Code | Description | Timing | Comments | # Loc Stage 4 | # Loc Stage 5 | # Loc Stage 6 | Scale |
|---|---|---|---|---|---|---|---|---|---|
| 1 | HS | RRG_R | Presence of RR gene | V2-V4, 4-7 DAYS AFTER SPRAYING | | Home Loc's | Home Loc's | Home Loc's | Roundup 1 = R, 5 = seg, 9 = susc, |
| 1 | HS | RUR_R | Roundup Tolerance Yellowing | R1-R2 | | Home Loc's | Home Loc's | Home Loc's | 1-9 scale, 1 = no yellowing, 9 is extreme yellowing |
| 1 | OTH | EMRGR | Emergence - stand establishment, uniformity and vigor | VE-V3 | NK EPA_R = V2-V6, 2005 on use EMRGR | | 2 | 4 | 1 to 9 (1 = best) |
| 2 | DIS | IC_R | Iron Deficiency Chlorosis | August | Internal Field Nursery | MG00-2L | MG00-4.9 | MG00-4.9 | 1 to 9 (1 = best) |
| 2 | DIS | ICFLR | Iron Deficiency Chlorosis Yellow Flash | Initial flash V2 June-July | Internal Field Nursery | MG00-2L | MG00-4.9 | MG00-4.9 | 1 to 9 (1 = best) |
| 2 | DIS | ICR_R | Iron Deficiency Chlorosis Recovery, (Stunting and/or Green-up) | 2-3 weeks after ICFLR | Internal Field Nursery | MG00-2L | MG00-4.9 | MG00-4.9 | 1 to 9 (1 = best) |
| 2 | DIS | PRR_R | Phytophthora Root Rot Tolerance in pond | Scheduled | Internal Field Nursery | | St. Joe | St. Joe | 1 to 9 (1 = best) for field tolerance |
| 2 | NEM | SCN_R | SCN Field Rating | June | Internal Field Nursery | | Conesville, St. Joe | Conesville, St. Joe | Field = 1-9 (1best) |
| 3 | AGR | FL_CR | Flower Color | R1 Confirmed | Numeric for EDC | Home Loc's | Home Loc's | Home Loc's | W = White; P = Purple; Seg = Mix |
| 3 | AGR | PLCNR | Plant canopy | August (~R5-R6) | Growth expressive locations. | | Opportunistic | Opportunistic | 1 to 9, 1 = Slender, 5 = Intermediate, 9 = Bush |
| 3 | DIS | ARSTR | Asian Rust Rating | When differences occur | | Opportunistic | Opportunistic | Opportunistic | 1 to 9 (1 = best) |
| 3 | DIS | BSR_R | Brown Stem Rot | When differences occur | | Opportunistic | Opportunistic | Opportunistic | 1 to 9 (1 = best) |
| 3 | DIS | CR_R | Charcoal Rot | When differences occur | | Opportunistic | Opportunistic | Opportunistic | 1 to 9 (1 = best) |
| 3 | DIS | DPC_R | Stem Canker (Northern) | When differences occur | | Opportunistic | Opportunistic | Opportunistic | 1 to 9 (1 = best) |
| 3 | DIS | DPM_R | Stem Canker (Southern) | When differences occur | | Opportunistic | Opportunistic | Opportunistic | 1 to 9 (1 = best) |
| 3 | DIS | FELSR | Frogeye Leaf Spot | When differences occur | | Opportunistic | Opportunistic | Opportunistic | 1 to 9 (1 = best) |
| 3 | DIS | SCL_R | Sclerotinia White Mold | When differences occur | | Opportunistic | Opportunistic | Opportunistic | 1 to 9 (1 = best) |
| 3 | DIS | SDS_R | Sudden Death Syndrome | When differences occur | | Opportunistic | Opportunistic | Opportunistic | 1 to 9 (1 = best) |
| 3 | PERF | GLDGR | Green lodging | R5 to R6 | Where differences occur | Opportunistic | Opportunistic | Opportunistic | 1 to 9 (1best) 1 = All erect; 5 = 45 degrees; 9 = flat |
| 4 | AGR | MRTYD | Maturity Date (MMDD)-95% of plants in row shed leaves & pods turned mature color | R8 | Home locations + 1-2 off site/ station | ~1-2 | ~5 | ~10 | MMDD (Sept 10 = 0910) |

-continued

Syngenta Soybean Data Collection Traits and Timing
Order 1 = Seedling, 2 = Vegetative, 3 = Reproductive to grain-fill, 4 = Maturity
Opportunistic ratings should only be collected if differences occur.
At least one variety has a rating of 5 or greater and there is a spread of 3 in the ratings.

| Order | Trait Group | Code | Description | Timing | Comments | # Loc Stage 4 | # Loc Stage 5 | # Loc Stage 6 | Scale |
|---|---|---|---|---|---|---|---|---|---|
| 4 | AGR | HC.CR | Hilum Color | R8 | Numeric for EDC | Home Loc's | Home Loc's | Home Loc's | G = Gray; BR = Brown; IB = Imperfect Black; Bl = Black; Y = Yellow; BF = Buff; IY = Imperfect Yellow; Seg = Mix |
| 4 | AGR | PB_CR | Pubescence Color | R8-Harvest | Numeric for EDC | Home Loc's | Home Loc's | Home Loc's | G = Gray; T = Tawny; LT = Lt. Tawny; Seg = Mix |
| 4 | AGR | PD_CR | Pod Color | R8-Harvest | Numeric for EDC | Home Loc's | Home Loc's | Home Loc's | T = Tan; B = Brown; Seg = Mix |
| 4 | AGR | PLBRR | Plant branching | R8-Harvest | Growth expressive locations. | Optional | Home Loc's | Home Loc's | 1 to 9, 1 = no branching; 5 = average branching; 9 = profuse branching |
| 4 | AGR | PLHTN | Plant Height (cm) | Harvest | Growth expressive locations. | Optional | Home Loc's | Home Loc's | Taken in cm |
| 4 | DIS | GS_R | Green Stem | Harvest | Where differences occur | Opportunistic | Opportunistic | Opportunistic | 1 to 9 (1 = best) |
| 4 | PERF | HLDGR | Harvest Lodging | R8-Harvest | Where differences occur | Opportunistic | Opportunistic | Opportunistic | 1 to 9 (1best) 1 = All erect; 5 = 45 degrees; 9 = flat |
| 4 | PERF | HVAPR | Harvest Appearance | Harvest | Where differences occur | Opportunistic | Opportunistic | Opportunistic | 1 to 9, 1 = Excellent, 5 = Avg, 9 = Poor |
| 4 | PERF | STR_R | Shattering | Harvest | Hill plot planter, 2006? | | Opportunistic + Bay and St. Joe | Opportunistic + Bay and St. Joe | 1 to 9 (1 = best) |

Roundup is a trademark of Monsanto
Trait Definitions
Opportunistic Ratings developed in YT. Opportunistic ratings should only be collected if differences occur. At least one variety has a rating of 5 or greater and there is a spread of 3 in the ratings. (Scale 1-9, 1 = Best).
Emergence (EMRGR) A rating of the uniform establishment and growth of seedlings. Taken from V1-V3, (Scale 1-9).
Maturity (MRTYD) The month and day (MMDD) when 95% of the main stem pods in the plot have reached their mature color.
Plant Height (PLHTN) The average measured plant height in cm.
Branching (PLBRR) Rating of the number of branches and their relative importance to yield. Taken at growth expressive locations. (Scale: 1-9, 1 = stick, no branching, 3 = 1 seed bearing branch, 5 = average branching 2-3 seed bearing branches, 7 = 3-4 seed bearing branches, 9 = profuse branching).
Green Lodging (GLDGR) Rating based on the average of plants leaning from vertical in R5 to R6 stage (Scale 1-9, 1 to 9 (1best) 1 = All erect; 5 = 45 degrees; 9 = flat).
Harvest Lodging (HLDGR) Rating based on the average of plants leaning from vertical at harvest (scale 1-9, 1 to 9 (1best) 1 = All erect; 5 = 45 degrees; 9 = flat).
Shatter (STR_R) Rating of pre-harvest loses based on amount of plants with open pods (Scale 1-9).
Iron Deficiency Chlorosis (IC_R) final rating = average of initial Yellow Flash (ICFLR) and recovery (ICR_R) taken 2-3 weeks after initial yellow flash. (Scale 1-9, 1 = Best). LS means analysis unequal entries and reps between years.
Soybean Cyst Nematode (CN_1R, CN_3R, CN_5R, CN14R) Greenhouse screen-30 day screen using infested soil. Rating Scale based upon female reproduction index on a susceptible check set where <10% = R; <30% = MR; <60% = MS; >60% = S. In priority order, the races screened include: 3, 14, 1 & 5.
Phytophthora Root Rot Field tolerance (PRR_R) or actual gene (RPS_T).
Sudden Death Syndrome (SDS_R) based on leaf area affected, scale 1-9. Can be GH or field.
Brown Stem Rot (BSR_R) Greenhouse pot--root dip or field rating of leaf symptoms. (Scale 1-9)
Root Knot Nematode Arenaria (MA_R), Incognita (MI_R). Javanica (MJ_R) RKN. Scale 1-9.
Stem Canker North (DPM_R) Southern (DPM_R). Scale 1-9.
Sulfentrazone (SUL_R) Greenhouse nursery rating damage of multiple rates. Scale 1-9.
Metributzin (MET_R) Greenhouse nursery rating damage of multiple rates. Scale 1-9.
Hypocotyl Elongation (HYP_R) A rating of a variety's hypocotyl extension after germination when planted at a 5" depth in sand and maintained a warm germination environment for 10 days. (Scale 1 = Long, 5 = Intermediate, 9 = Short)

Trait Definitions

Hypocotyl Elongation (HYPO) A rating of a variety's hypocotyl extension after germination when planted at a 5" depth in sand and maintained a warm germination environment for 10 days.

Seedling Establishment (EMG) A rating of the uniform establishment and growth of seedlings.

Maturity (MAT) The number of days after Aug. 31 when 95% of the main stem pods in the plot have reached their mature color.

Peroxidase Activity (Perox)—seed protein peroxidase activity is defined as a chemical taxonomic technique to separate cultivars based on the presence or absence of the peroxidase enzyme in the seed coat. Ratings are POS=positive for peroxidase enzyme or NEG=negative for peroxidase enzyme.

Plant Height (PLTHT) The average measured plant height in centimeters.

Branching (BRANCH or PLBRR) Rating of the number of branches and their relative importance to yield. This rating is taken at growth expressive locations.

Green Lodging (GLODGE or GLDGR) Rating based on the average of plants leaning from vertical in R5 to R6 stage.

Stem Lodging (LODGE) Rating based on the average of plants leaning from vertical at harvest. Lodging score (1=completely upright, 9=completely prostrate), Shatter (SHAT or STR_R) Rating of pre-harvest loses based on amount of plants with open pods.

Iron Deficiency Chlorosis (IDC or IC_R) A composite rating of Yellow Flash, Green-up, and Stunting in HpH soil. A 1 rating is the most positive for resistance to the symptoms listed and 9 is the least positive.

*Phytophthora* Root Rot (PGR) or (PFT) Greenhouse pot—root dip method for PFT and hypodermic needle method for rating PGR.

Root Knot Nematode (RKN) Greenhouse screen—30 day screen using infested soil. Rating Scale based upon female reproduction index on a susceptible check set where <10%=R; <30%=MR; <60%=MS; >60%=S.

Stem Canker (STC) Based on number of lesions, scale 1-5.

Sulfentrazone (SULF) Authority™ (commercial herbicide) Greenhouse nursery rating damage of multiple rates.

Metributzin (MET) Greenhouse nursery rating damage of multiple rates.

Definitions of Staging of Development

The plant development staging system employed in the testing of this invention divides stages as vegetative (V) and reproductive (R). This system accurately identifies the stages of any soybean plant. However, all plants in a given field will not be in the stage at the same time. Therefore, each specific V or R stage is defined as existing when 50% or more of the plants in the field are in or beyond that stage.

The first two stages of V are designated a VE (emergence) and VC (cotyledon stage). Subdivisions of the V stages are then designated numerically as V1, V2, V3 through V (n). The last V stage is designated as V (n), where (n) represents the number for the last node stage of the specific variety. The (n) will vary with variety and environment. The eight subdivisions of the reproductive stages (R) states are also designated numerically. R1=beginning bloom; R2=full bloom; R3=beginning pod; R4=full pod; R5=beginning seed; R6=full seed; R7=beginning maturity; R8=full maturity.

BROWN STEM ROT (BSR)—This disease is caused by the fungus *Phialophora gregata*. The disease is a late-season, cool-temperature, soilborne fungus which in appropriate favorable weather can cause up to 30 percent yield losses in soybean fields. For purposes of these tests the information is gathered in a greenhouse with a plant in a pot then a root dip procedure is employed.

SUDDEN DEATH SYNDROME (SDS or SDS_R)—This disease is caused by slow-growing strains of *Fursarium solani* that produce bluish pigments in culture. The disease is a mid to late season, soil borne disease that occurs in soybean fields with high yield potential. Yield losses may be total or severe in infected fields. Sudden Death Syndrome (SDS) is based on leaf area affected. The scale used for these tests is 1-5 or if identified as SDS_R the scale is 1-9.

SOYBEAN CYST NEMATODE—The Soybean Cyst Nematode (SCN) *Heterodera glycines*, is a small plant-parasitic roundworm that attacks the roots of soybeans. Soybean Cyst Nematode (SCN) for purposes of these tests is done as a greenhouse screen—30 day screen using infested soil. The rating scale is based upon female reproduction index on a susceptible check set where <10%=R (RESISTANT); <30%=MR (MODERATELY RESISTANT); <60%=MS (MODERATELY SUSPECTIBLE); >60%=S (SUSPECTIBLE). In priority order, the screening races include: 3, 14, & 1.

MATURITY DATE. Plants are considered mature when 95% of the pods have reached their mature color. The number of days is either calculated from August 31 or from the planting date. (MR#) wherein # equals days.

RELATIVE MATURITY GROUP (RM). Industry Standard for varieties groups, based day length or latitude. Long day length (northern areas in the Northern Hemisphere) is classified as (Groups 000, 00, 0,). Mid day lengths variety groups lie in the middle (Groups I-VI). Very short day lengths variety groups (southern areas in Northern Hemisphere) are classified as (Groups VII, VIII, IX).

SEED YIELD (Bushels/Acre). The yield in bushels/acre is the actual yield of the grain at harvest.

SHATTERING. The rate of pod dehiscence prior to harvest. Pod dehiscence involves beans dropping out of the pods. Shatter (SHAT) for these tests the rating of pre-harvest loses is based on amount of plants with open pods.

PLANT. Means the plant, the plant's cells, plant protoplasts, plant cells of tissue culture from which soybean plants can be regenerated, plant calli, plant clumps, and plant cells that are intact in plants or parts of the plants, such as pollen, nodes, roots, flowers, seeds, pods, leaves, stems, pod and the like.

The present invention is S06-WW157958 a Maturity Group III soybean. This soybean is developed for use of the beans. S06-WW157958 is adapted for the upper Midwest where other Maturity Group III soybeans are grown. This soybean variety does carry *Phytophthora* Root Rot resistance in the form of the Rsp 1 k gene.

This soybean variety in one embodiment carries one or more transgenes, for example, the glyphosate tolerance transgene, a desaturase gene or other transgenes. In another embodiment of the invention does not carry any herbicide resistance traits. In yet another embodiment of the invention, the soybean does not carry any transgenes but carries alleles for aphid resistance, cyst nematode resistance and/or brown stem or the like.

The traits of the invention are listed below.

Traits

| Plant Characteristics | |
|---|---|
| RR ® | Y |
| STS ® | N |
| Flower Color | W |
| Pubescence Color | LT |
| Pod Color | B |
| Hilum Color | BL |
| % Protein 13% mst. | 34.3 |
| % Oil @ 13% mst. | 20.0 |
| Seed Size/Lb | 2792.0 |
| Stem Termination | 2.0 |
| Plant Health | |
| Rps Gene | 1K |
| Phytopthora Root Rot Tolerance | 4.0 |
| SCN RACE 1 FI % | |
| SCN RACE 3 FI % | |
| SCN RACE 5 FI % | |
| SCN RACE 14 FI % | |
| Root Knot Nematode - Incognita | |
| Root Knot Nematode - Arenaria | |
| Stem Canker (Southern) | |
| Stem Canker Tolerance (Southern) | |

Rps gene indicates the specific gene for resistance but if none are indicated then none are known to be present
Y = Yes, has trait. N = no does not contain trait
SCN = Soybean Cyst Nematode
Roundup Ready ®, Roundup ® and Roundup ® Ultra are trademarks of Monsanto Company. STS ® is a trademark of DuPont.
Ratings are on a 1 to 9 scale with 1 being the best.

The instant invention provides methods and composition relating to plants, seeds and derivatives of the soybean cultivar S06-WW157958. Soybean cultivar S06-WW157958 has superior characteristics. The S06-WW157958 line has been selfed sufficient number of generations to provide a stable and uniform plant variety.

Cultivar S06-WW157958 shows no variants other than expected due to environment or that normally would occur for almost any characteristic during the course of repeated sexual reproduction. Some of the criteria often used to select in various generations include: seed yield, emergence, appearance, disease tolerance, maturity, plant height, and shattering data.

The inventor believes that S06-WW157958 is similar to the comparison varieties shown in the last table. However, as shown in the table, S06-WW157958 differs from these cultivars.

Direct comparisons were made between S06-WW157958 and the listed commercial varieties. Traits measured included yield, maturity, moisture, lodging, plant height, branching, field emergence, and shatter. The results of the comparison are presented in below. The number of tests in which the varieties were compared is shown with the environments, mean and standard deviation for some traits.

The present invention S06-WW157958 can carry genetic engineered recombinant genetic material to give improved traits or qualities to the soybean. For example, but not limitation, the present invention can carry, the glyphosate resistance gene for herbicide resistance as taught in the Monsanto patents (WO92/00377, WO92104449, U.S. Pat. No. 5,188,642 and U.S. Pat. No. 5,312,910) or STS mutation for herbicide resistance. Additional traits carried in transgenes or mutation can be transferred into the present invention. Some of these genes include genes that give disease resistance to sclerotina such as the oxalate oxidase (Ox Ox) gene as taught in PCT/FR92/00195 Rhone Polunc and/or an Oxalate Decarboxylase gene for disease resistance or genes designed to alter the soybean oil within the seed such as desaturase, thioesterase genes (shown in EP0472722, U.S. Pat. No. 5,344,771) or genes designed to alter the soybean's amino acid characteristics. This line can be crossed with another soybean line that carries a gene that acts to provide herbicide resistance or alter the saturated and/or unsaturated fatty acid content of the oil within the seed, or the amino acid profile of the seed.

The present invention S06-WW157958 is employed in a number of plot repetitions to establish trait characteristics. The present invention is grown in a number of regions for testing and researching the invention in various environmental interactions.

Geographic Summary

Figure 1:
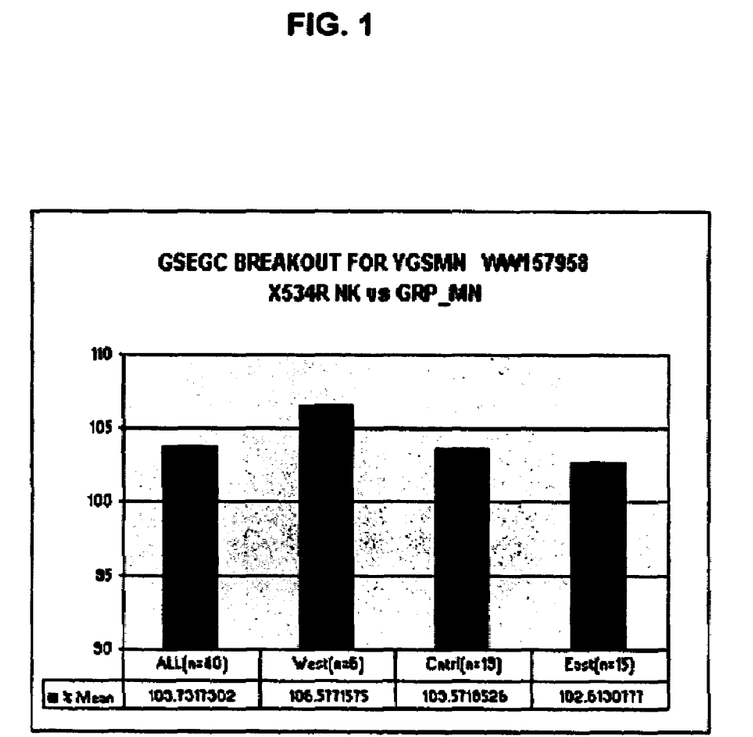
FIG. 1 shows the Geographic Segment Chart—GSEGC shows the breakout for grain yield at standard moisture for S06-WW157958 across geographic locations.

The target variety yield is given as a percent of the trial average at all locations shown in FIG. 1 and each geographic segment West to East or Central (Cntrl) to South East where there are three or more locations. The plots for these trials are 17.5 plots with 30-inch rows. The plants in the plots are a combination of experimental material and commercial material. There are usually 36 varieties and there are approximately 300 plants of each variety with two replications in 20-25 locations. The data in FIG. 1 is only charted if there are at least 3 or more locations. N>=3

The present invention at 103.73 differs from the comparison commercial soybean lines in that it is exceeding the mean of the group of soybeans (GRP_MN) that were tested and displayed in this geographic segment chart (GSEGC). When looking at the East region the present invention is showing a 102.61 yield and in the Central region the present invention has a 103.57 yield as shown in FIG. 1. But the powerhouse of yield is evidenced in the West region where the present invention is at 106.57 as shown in FIG. 1. This invention also works well in the West.

Figure 2:
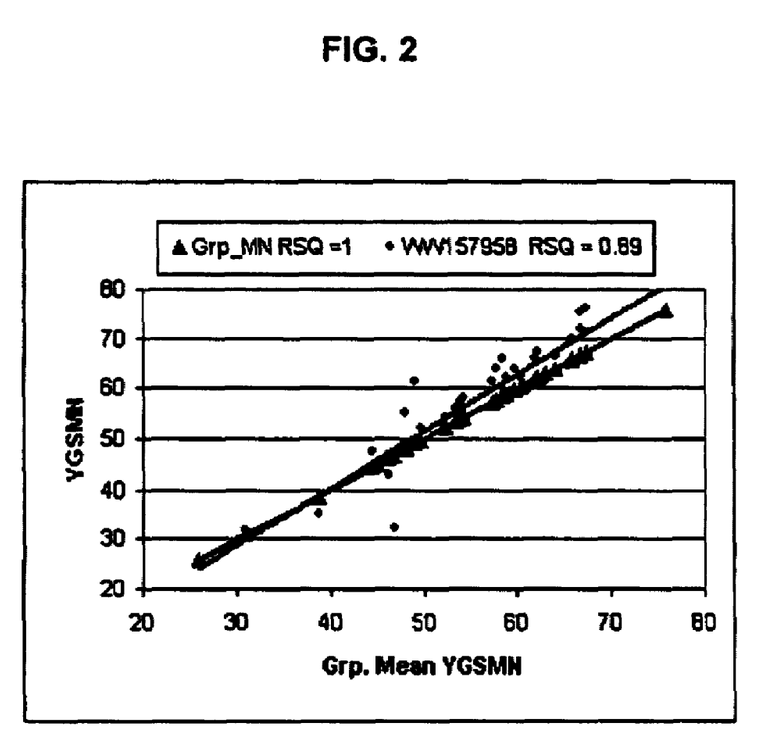
FIG. 2 shows the Group Mean chart (GRP MN=Group Mean) of Grain Yield at standard moisture for S06-WW157958. This chart shows Yield Stability–Win>5% of trial mean, Tie +or –5% of the trial mean, Loses <5% of trial mean. The chart's vertical axis=yield of target variety, its horizontal axis=location average yield. When the target variety line is a above the location average line is desirable. The RSQ of the target variety shows a number. This number when it is closest to 1=yield stability.

The present invention S06-WW157958 (identified herein as WW157958) is employed in a trial for testing a number of environments. The results of the grain yield at standard moisture are shown in the chart as shown in FIG. 2. The present invention is a variety that will yield most soybeans in a high yielding environment and in a mid yielding environment. If the environment is extremely low yielding the present invention tends to under achieve in its performance when compared to the group mean.

The RSQ is showing a low number. Since the outlaying data points are primarily above the Group Mean or within the Group Mean the low number for RSQ is acceptable. These tests allow the usefulness of the invention to be shown in light of the environmental genetic interactions.

Research Data 2004-2005 Yield Performance Chart

| VHNO | YGSMN | MRTYN | HLDGR | PLHTN | PRR_R | IC_R | SDS_R | SCL_R | FELSR | STR_R | GLDGR | PLBRR | EMRGR |
|---|---|---|---|---|---|---|---|---|---|---|---|---|---|
| Commercial-1 | 58.4 | 133.4 | 3.4 | 94.8 | 3.8 | 5.8 | 4.8 | 5.5 | | 2.1 | 3.9 | | 3.1 |
| S28-G1 | 58.1 | 130.7 | 2.9 | 83.6 | 4.4 | 5.6 | 4.3 | 3.5 | | 3.5 | 4.6 | | 3.4 |
| WW157958 | 58.0 | 134.7 | 4.4 | 95.0 | 3.5 | 5.4 | 4.1 | 4.5 | | 3.0 | 5.0 | | 2.9 |
| Environments | 40.0 | 17.0 | 25.0 | 12.0 | 2.0 | 2.0 | 7.0 | 1.0 | | 3.0 | 1.0 | | 6.0 |
| Mean | 58.2 | 133.0 | 3.6 | 91.1 | 3.9 | 5.6 | 4.4 | 4.5 | | 2.9 | 4.5 | | 3.1 |
| LSD (0.05) | | 1.0 | 0.4 | 3.4 | | | | | | | | | |

Each of these lines has their own positive traits. Each of these lines is different from the present invention. The present invention has lower yield at standard moisture than do the two of comparison lines. The present invention shows a good rating for emergence. The sudden death syndrome rating is the lowest for all of the lines. The yield and other data is a snapshot of each of these lines' results in the specific environment and will differ when other environmental interactions are measured.

This invention also is directed to methods for producing a new soybean plant by crossing a first parent plant with a second parent plant wherein the first or second parent plant is the present invention. Additionally, the present invention maybe used in the variety development process to derive progeny in a breeding population or crossing. Further, both first and second parent plants can come from the soybean line S06-WW157958. A variety of breeding methods can be selected depending on the mode of reproduction, the trait, and the condition of the germplasm. Thus, any such methods using the S06-WW157958 are part of this invention: selfing, backcrosses, recurrent selection, mass selection and the like.

The scope of the present invention includes any use on S06-WW157958 of marker methods. Through the use of markers such as SSRs, RFLP's, SNPs, Ests, AFLPs, gene primers, and the like to identify genetic alleles which can be identified and breed with marker assistance into the present invention with little to no superfluous germplasm being dragged into the present invention. This results in formation of the present invention plus for example, cyst nematode resistance, brown stem rot resistance, aphid resistance, phytothora resistance, IDC resistance, BT genes or male sterility genes or glyphosate tolerance genes or drought tolerance genes or alleles and the like. Transgenes maybe directly introduced into cultivar using genetic engineering and transformation techniques well known in the art, some of which are described above, or are originally introduced into a donor, parent using genetic engineering and transformation techniques, and using the donor in a marker assisted trait conversion process, the trait is moved for example by backcrossing. A transgene typically comprises a nucleotide sequence whose expression is responsible or contributes to the trait, under the control of a promoter capable of directing the expression of the nucleotide sequence at the desired time in the desired tissue or part of the plant. Constitutive, tissue-specific or inducible promoters all have different purposes and each could be employed. The transgene may also comprise other regulatory elements such as for example translation enhancers or termination signals. The transgene may be adapted to be transcribed and translated into a protein, or to encode RNA in a sense or antisense orientation such that it is not translated or only partially translated.

The scope of the present invention also includes any use on S06-WW157958 of transformation methods. Transformation methods are means for integrating new genetic coding sequences (transgenes) into the plant's genome by the incorporation of these sequences into a plant through man's assistance. Many dicots including soybeans can easily be transformed with *Agrobacterium*. Methods of introducing desired recombinant DNA molecule into plant tissue include the direct infection or co-cultivation of plant cells with *Agrobacterium tumefaciens*, Horsch et al., Science, 227: 1229 (1985). Descriptions of *Agrobacterium* vector systems and methods are shown in Gruber, et al., "Vectors for Plant Transformation, in Methods in Plant Molecular Biology & Biotechnology" in Glich et al., (Eds. pp. 89-119, CRC Press, 1993). Transformed plants obtained via protoplast transformation are also intended to be within the scope of this invention. The most common method of transformation after the use of *agrobacterium* is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art. The DNA used for transformation of these plants clearly may be circular, linear, and double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular are well known in the art. The plants from the transformation process or the plants resulting from a cross using a transformed line or the progeny of such plants are transgenic plants that carry the transgene.

DEPOSIT INFORMATION

Applicants have made a deposit of at least 2500 seeds of soybean cultivar S06-WW157958 with the American Type Culture Collection (ATCC), Manassas, Va. 20110 on May 9, 2007 and designated PTA-8413. The seeds were tested on May 21, 2007 and found to be viable. Access to this deposit will be available during the pendency of the application to the Commissioner for Patents and persons determined by the Commissioner to be entitled thereto upon request. Upon granting of a patent on any claims in the application, the Applicants will make the deposit available to the public pursuant to 37 CFR §1.808. Additionally, Applicants will meet the requirements of 37 CFR §1.801-1.809, including providing an indication of the viability of the sample when the deposit is made. The ATCC deposit will be maintained in that depository, which is a public depository, for a period of 30 years, or 5 years after the last request, or for the effective life of the patent, whichever is longer, and will be replaced if it becomes nonviable during that period.

Accordingly, the present invention has been described with some degree of particularity directed to the preferred embodiment of the present invention. It should be appreciated, though that the present invention is defined by the following claims construed in light of the prior art so that modifications or changes may be made to the preferred embodiment of the present invention without departing from the inventive concepts contained herein.

What is claimed is:

1. A soybean seed designated S06-WW157958, a sample of said seed deposited under ATCC Accession No. PTA-8413.

2. A plant, or parts thereof, produced by growing the seed of claim 1.

3. Pollen of the plant of claim 2.

4. A soybean plant, or parts thereof, having all of the physiological and morphological characteristics of the soybean plant of claim 2.

5. A tissue culture of regenerable cells of the soybean plant of claim 2.

6. The tissue culture according to claim 5, wherein the cells are obtained from the group consisting of leaf, pollen, embryo, meristematic cell, root, root tip, anther, stomatal cell, flower, seed, stem and pod.

7. A soybean plant regenerated from the tissue culture of claim 6, having all of the morphological and physiological characteristics of soybean cultivar S06-WW157958.

8. A method for producing a soybean seed comprising crossing two soybean plants and harvesting the resultant soybean seed, wherein at least one soybean plant is the soybean plant of claim 2.

9. A method for producing a hybrid soybean seed comprising crossing the soybean plant according to claim 2 with a second soybean plant and harvesting the resultant hybrid soybean seed.

10. A method for producing a S06-WW157958-derived soybean plant, comprising:
    a) crossing soybean line S06-WW157958, a sample of said line deposited under ATCC Accession No. PTA8413, with a second soybean plant to yield progeny soybean seed; and
    b) growing said progeny soybean seed to yield said S06-WW157958-derived soybean plant.

11. The method of claim 8, wherein the second soybean plant is transgenic.

12. The method of claim 11 wherein the transgenic soybean plant contains genetic material selected from the group consisting of herbicide resistance, nematode resistance, insect resistance, resistance to disease, and male sterility.

13. The method of claim 12 wherein the resistance to disease is through an oxalate oxidase encoding polynucleotide sequence or an oxalate decarboxylase encoding polynucleotide sequence.

* * * * *